United States Patent [19]

Jarque et al.

[11] 4,000,283
[45] Dec. 28, 1976

[54] COMPOUND 3,4,5-TRIMETHOXYPHENYL-(3,4-DIMETHYL-2-PYRIDYL)-CARBONYL

[75] Inventors: Ricardo Granados Jarque; Juan Bosch Cartés; Jorge Canals Cabiró, all of Barcelona; Cristobal Martinez Roldán; Fernando Rabadán Peinado, both of Madrid, all of Spain

[73] Assignee: Laboratorios Made, S.A., Spain

[22] Filed: Apr. 29, 1975

[21] Appl. No.: 572,862

[30] Foreign Application Priority Data

May 4, 1974 Spain .............................. 425972

[52] U.S. Cl. .......................... 424/263; 260/297 R
[51] Int. Cl.$^2$ .............. C07D 211/70; A61K 31/44
[58] Field of Search ................ 260/297 R; 424/263

[56] References Cited
OTHER PUBLICATIONS

Sankey et al., J. of *Heterocyclic Chem.* (1972), vol. 9 (5), pp. 1049–1055.
*Chemical Abstracts,* vol. 78 (1973) 4088.

*Primary Examiner*—Henry R. Jiles
*Assistant Examiner*—Bernard Dentz
*Attorney, Agent, or Firm*—Marn & Jangarathis

[57] ABSTRACT

The compound 3,4,5-trimethoxyphenyl-(3,4-dimethyl-2-pyridyl carbinol and pharmaceutically acceptable acid addition salts thereof.

3 Claims, No Drawings

COMPOUND 3,4,5-TRIMETHOXYPHENYL-(3,4-DIMETHYL-2-PYRIDYL)-CARBONYL

The present invention relates to a method for the production of 1,3,4-trimethyl-2-(3,4,5-trimethoxybenzyl)-1,2,5,6-tetrahydropyridine of formula (I), its addition salts with pharmaceutically acceptable acids, and an intermediate for the preparation of the compound of formula I, namely 3,4,5-trimethoxyphenyl-(3,4-dimethyl-2-pyridyl)-carbinol of formula (II)

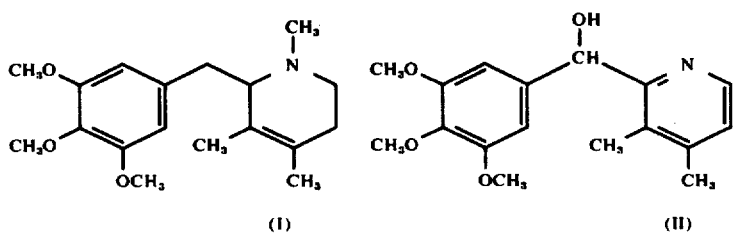

The above-mentioned compounds are novel pharmaceutical substances, useful as analgesics against inflammation and in accordance with the method of the invention they are obtained according to the following sequence of reactions:

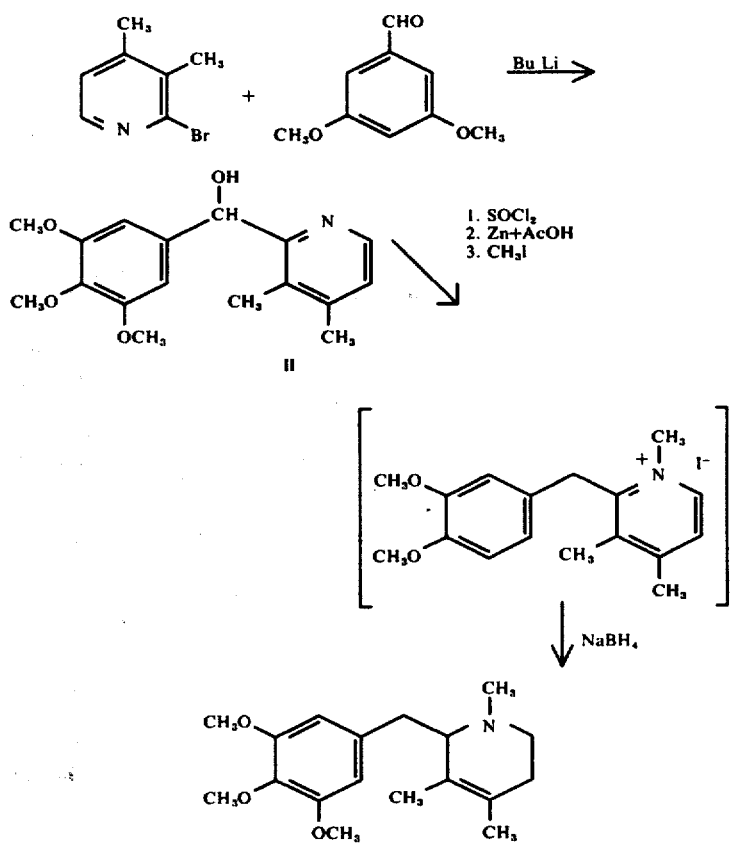

In the first part of the process 3,4,5-trimethoxybenzaldehyde is reacted with 2-bromo-3,4-dimethylpyridine under an inert atmosphere in solution in ether and in the presence of freshly prepared butyl-lithium. The reaction is performed at a temperature of about $-40°$ C maintained in the addition of butyl-lithium to the 2-bromo-3,4-dimethylpyridine, about $-25°$ C during the addition of the solution of 3,4,5-trimethoxybenzaldehyde in anhydrous benzene, about $-15°$ C in the course of the reaction, and finally ambient temperature at the end of the process. The resulting mixture is poured over dilute hydrochloric acid and ice, the acid layer is neutralized with a current of ammonia, precipitating the 3,4,5-trimethoxybenzyl-(3,4-dimethyl-2-pyridyl)-carbinol (II).

In the second phase of the present invention, the previously prepared carbinol (II) is converted into the tetrahydropyridine (I) without isolating any of the intermediate compounds. For this, the compound of formula (II) is made to react in the first instance with thionyl chloride, maintaining the temperature below $20°$ C. Subsequently the chloride thus obtained is dissolved in glacial acetic acid and is reduced with zinc powder. The acetic acid is eliminated by evaporation under vacuum, and the residue is extracted with ether after being made alkaline. Concentration of the ether layer leads to an oil which, dissolved in methanol, is treated with methyl iodide to provide a pasty residue which corresponds to 1,3,4-trimethyl-2-(3,4,5-trimethoxybenzyl)-pyridinium iodide.

The said intermediate is made to react with sodium borohydride in the presense of methanol. After diluting with water, extracting with ether, and evaporating the ether solution, an oil (I) is obtained, from which the hydrochloride is precipitated, which is purified by crystallization from acetone.

The present invention is illustrated without limitation in the following examples:

EXAMPLE 1

Production of 3,4,5-trimethoxyphenyl-(3,4-dimethyl-2-pyridyl) carbionol (II)

40 g of 2-bromo-3,4-dimethylpyridine dissolved in 50 ml of anhydrous ether are slowly added, with agitation and under a nitrogen atmosphere, to 300 ml of a 0.9 M solution of butyl-lithium in ether cooled to −40° C. The resulting mixture is agitated for 2 hours at this temperature, and 50 g of 3,4,5-trimethoxybenzaldehyde dissolved in 200 ml of anhydrous benzene are added, and the mixture kept at a temperature below −25° C. Agitation is performed for 1 hour at −15° C, and the reaction is continued until ambient temperature is reached. The mixture is poured on to ice and dilute hydrochloric acid, the acid layer is made alkaline with a current of ammonia, while cooling externally with ice. The precipitate is collected by filtration, supplying 62.6 g of (II). Yield 96%. An analysis sample is crystallized from alcohol (m.p. = 104–6° C). Analysis: $C_{17}H_{21}NO_4$. Calculated: C = 67.31, H = 6.98, N = 4.62. Found: C = 67.23, H = 7.33, N = 4.57.

EXAMPLE 2

Production of 1,3,4-trimethyl-2-(3,4,5-trimethoxybenzyl)-1,2,5,6-tetrahydropyridine (I) and its hydrochloride 5.3 g of thionyl chloride are added dropwise to a solution of 11.3 g of (II) in 45 ml benzene, the temperature being kept below 20° C. The mixture is agitated for 1 hour at ambient temperature and then made alkaline with a 25% aqueous solution of sodium hydroxide. The organic layer is dried and evaporated, supplying 10 g of a residue. The residue is dissolved in 45 ml of glacial acetic acid and is reduced by slowly adding 6 g of powdered zinc, while stirring. The mixture is heated under reflux and agitation for 4 hours, cooled and the inorganic salts filtered off. The acetic acid is removed by distillation under vacuum. The resulting residue is made alkaline with a 25% aqueous solution of sodium hydroxide and is extracted with ether. The ether layer is dried and concentrated, yielding an oil which is purified by distillation, to give 7.8 g of a viscous liquid, with boiling point 166°–185° C / 0.06 mm Hg, which corresponds to the intermediate 2-(3,4,5-trimethoxybenzyl)-3,4-dimethylpyridine.

6 ml of methyl iodide are added slowly to the distillate, dissolved in 35 ml of methanol, while stirring at ambient temperature for 1 hour, and then under reflux for a further 3 hours. The solvent is evaporated to leave a pasty residue which is washed with anhydrous benzene. The residue is dissolved in 30 ml methanol, and 0.3 g of sodium borohydride is added with cooling. The mixture is heated under reflux for 6 hours, at the end of which it is diluted with water, and extracted several times with ether. From the dried ether layer, the hydrochloride is precipitated with a solution of dry hydrochloric acid in ether. The precipitate is crystallized from acetone, in a yield of 4.4 g, m.p. = 221°–223° C. Total yield of the process = 34%. Analysis: $C_{18}H_{28}NO_3Cl$. Calculated: C = 63.24, H = 8.25, N = 4.09, Cl = 10.37. Found: C = 63.18, H = 8.45 N = 4.26, Cl = 10.12.

PROPERTIES OF THE PRODUCTS OF THE INVENTION

Products

I — 1,3,4-trimethyl-2-(3,4,5-trimethoxybenzyl)-1,2,5,6-tetrahydropyridine.

II — 3,4,5-trimethoxyphenyl-(3,4-dimethyl-2-pyridyl)carbinol.

They are products with analgesic activity. Dextropropoxyphene was used as comparison analgesic.

A — ACUTE TOXICITY

The acute toxicity studies were carried out in albino I.C.R. Swiss mice weighing 30 ± 2 g, of both sexes. The products were administered intraperitoneally (i.p). The acute toxicity was calculated according to the method of Litchfield and Wilcoxon.

TABLE A

| Products | $LD_{50}$ | |
|---|---|---|
| I | 154.5 | mg/kg |
| II | 292 | mg/kg |
| Dextropropoxyphene | 140 | mg/kg |

As may be observed, products I and II are less toxic than dextropropoxyphene.

B — ANALGESIA

The analgesic action was investigated in albino I.C.R. Swiss mice, using the acetic acid-induced writhing technique. Groups each of 10 mice were assembled.

The analgesics were injected intraperitoneally (i.p), and after 30 minutes 0.25 ml of a 1% solution of acetic acid was injected i.p. A control group received acetic acid only. The number of writhes made by each mouse was counted during the 20 minutes following the administration of acetic acid.

TABLE B-I

| Treatment | Dose | No. of writhes (x ± M.S.E.)[1] | P |
|---|---|---|---|
| Product I | 20 mg/kg | 74.5 ± 4.84 | p < 0.001 |
| Dextropropoxyphene | 25 mg/kg | 22.8 ± 4.74 | p < 0.001 |
| Control | — | 112.1 ± 4.2 | — |

[1] Average value ± mean standard error

Product I has analgesic activity but less than that of dextropropoxyphene.

TABLE B-II

| Treatment | Dose | Number of writhes (x ± M.S.E.) | P |
|---|---|---|---|
| Product II | 40 mg/kg | 29 ± 7.3 | p < 0.001 |
| Dextropropoxyphene | 25 mg/kg | 50.2 ± 4.4 | p < 0.001 |
| Control | — | 99.6 ± 5.6 | — |

Product II has high analgesic activity and with the same therapeutic index as dextropropoxyphene.

Examples are given below of pharmaceutical compositions in which there appear as active components the following products, associated with pharmaceutical vehicles and excipients.

I — 1,3,4-trimethyl-2-(3,4,5-trimethoxybenzyl)-1,2,5,6-tetrahydropyridine and its hydrochloride.

II — 3,4,5-trimethoxyphenyl-(3,4-dimethyl-2-pyridyl)-carbinol.

The daily oral dose of Product I is 2.23 mg per kg weight. A person weighing 70 kg would be administered 150 mg per day, distributed over three doses of 50 mg.

The daily oral dose of product II is 4.46 mg per kg weight. A person weighing 70 kg would be administered 300 mg per day, distributed over 3 doses of 100 mg.

EXAMPLE 1

| Hard gelatine capsules | |
|---|---|
| 1,3,4-trimethyl-2-(3,4,5-trimethoxybenzyl)-1,2,5,6-tetrahydropyridine (or its hydrochloride) | 50 mg |
| Lactose | 100 mg |
| Magnesium stearate | 2.5 mg |

EXAMPLE 2

| Injectable solution. Composition per ampoule: | |
|---|---|
| 1,3,4-trimethyl-2-(3,4,5-trimethoxybenzyl)-1,2,5,6-tetrahydropyridine hydrochloride | 35 mg |
| Sodium chloride | 27 mg |
| Sodium metabisulphite | 3 mg |
| Water for injectables 9.S.P. | 3 ml |

EXAMPLE 3

| Hard gelatine capsules. Composition per capsule: | |
|---|---|
| 3,4,5-trimethoxyphenyl-(3,4-dimethyl-2-pyridyl)-carbinol | 100 mg |
| Lactose | 50 mg |
| Magnesium stearate | 2.5 mg |

We claim:
1. The compound 3,4,5-trimethoxyphenyl-(3,4-dimethyl-2-pyridyl)-carbinol and pharmaceutically acceptable acid addition salts thereof.
2. A pharmaceutical composition exhibiting analgesic properties which comprises an analegesically effective amount of a compound selected from the group consisting of 3,4,5-trimethoxyphenyl-(3,4-dimethyl-2-pyridyl)-carbinol and pharmaceutically acceptable acid addition salts thereof and a pharmaceutically acceptable carrier therefor.
3. A process for treating an animal comprising administering to the animal an analgesically effective amount of a compound selected from the group consisting of 3,4,5-trimethoxyphenyl-(3,4-dimethyl-2-pyridyl)-carbinol and pharmaceutically acceptable acid addition salts thereof.

* * * * *